US005362569A

United States Patent [19]
Bauman

[11] Patent Number: 5,362,569
[45] Date of Patent: Nov. 8, 1994

[54] ANODIZING AND DUPLEX PROTECTION OF ALUMINUM COPPER ALLOYS

[76] Inventor: Albert J. Bauman, 524 Oakdale Dr., Sierra Madre, Calif. 91024

[21] Appl. No.: 34,291

[22] Filed: Mar. 22, 1993

[51] Int. Cl.[5] .......................... B32B 15/04; B32B 15/20

[52] U.S. Cl. .................................. 428/472.2; 148/275; 148/272; 205/50; 205/201; 205/204; 205/213; 205/329; 205/330; 205/332; 205/188

[58] Field of Search ................. 205/50, 317, 324, 213, 205/329, 330, 332, 201, 204, 229, 188; 148/248, 251, 252, 274, 275, 276, 277

[56] References Cited

U.S. PATENT DOCUMENTS

| | | | |
|---|---|---|---|
| 3,716,421 | 2/1973 | Burkhart et al. | 148/269 |
| 5,169,458 | 12/1992 | Shulman et al. | 148/248 |

*Primary Examiner*—John Niebling
*Assistant Examiner*—Edna Wong
*Attorney, Agent, or Firm*—Louis J. Bachand

[57] ABSTRACT

Copper alloys of aluminum are afforded extended protection against surface corrosion by anodizing the aluminum surface to be protected, treating the surface with a heterocyclic aromatic azole treating agent having up to 16 carbon atoms before, during or after the anodizing step, and coating the treated surface after anodize with a fatty acid of 5 to 24 carbon atoms.

27 Claims, No Drawings

ANODIZING AND DUPLEX PROTECTION OF ALUMINUM COPPER ALLOYS

TECHNICAL FIELD

This invention relates to corrosion protection of aluminum alloys with copper, and more particularly to the protection of aluminum alloys with copper as the principal though minor alloying ingredient by the application of a protective layer comprising anodize, fatty acid and a heterocyclic aromatic azole treating agent. Tests have shown that a synergistic improvement in corrosion resistance is obtained by combining the treating agent with fatty acid on anodized aluminum alloy panels, over the results obtained by either a fatty acid or the treating agent combined with anodize alone. Panels prepared in accordance with the invention have shown corrosion resistance in standard salt spray tests for over 4000 hours, more than ten times the MilSpec requirement of 336 hours.

BACKGROUND ART

Aluminum alloys with copper, e.g. the Series 1000, 2000 and 7000 aluminum alloys, are extensively used in architectural, aircraft and marine applications, and as such are desirably improved in corrosion resistance without adverse trade-offs such as increased weight or discoloration. At the same time, increasing environmental concerns dictate that improvements be obtained without undue use of environmentally hazardous chemicals in anodizing, such as chromates.

In U.S. Pat. No. 5,169,458 to Shulman and Bauman, improvements in corrosion resistance of aluminum were obtained by conditioning a freshly anodized aluminum surface with alcohol and treating with a fatty acid. Corrosion resistance to as much as 2856 hours was obtained using stearic acid and isopropyl alcohol.

DESCRIPTION OF THE INVENTION

It is an object therefore of the present invention to further improve the corrosion resistance of aluminum, specifically aluminum alloys with copper, beyond levels previously achieved. It is another object to employ an azole treating agent in combination with anodize and fatty acid treatments of aluminum copper alloy surfaces.

These and other objects of the invention to become apparent hereinafter are realized in accordance with the method of protecting copper alloys of aluminum against surface corrosion, including anodizing the aluminum surface to be protected, treating the surface with a heterocyclic aromatic azole treating agent having up to 16 carbon atoms before, during or after the anodizing step, and coating the treated surface after the anodizing step with a fatty acid of 5 to 24 carbon atoms.

In preferred embodiments, the method includes selecting an aluminum alloy of the 1000, 2000, or 7000 series; anodizing the aluminum surface to an anodize layer thickness of 0.2 to 0.6 mils selecting benzotriazole-5-carboxylic acid as the treating agent; treating the aluminum surface with any of three application methods: an organic solution of the treating agent in advance of anodizing the surface; or, adding the treating agent to an anodizing bath, and anodizing the surface in the bath while simultaneously treating the surface with the treating agent; or treating the anodized surface with an organic solution of the treating agent after the anodizing step. Alternatively, simultaneously treating the anodized surface with treating agent and coating the surface with the fatty acid; from an alcoholic solution and/or forming a common solution of the treating agent and the fatty acid for coating the surface.

In a more particularly preferred embodiment, the invention provides the method of protecting series 1000, 2000 and 7000 copper-containing alloys of aluminum against surface corrosion, which includes pretreating the bare metal surface with a 1 to 10% by weight solution in a hydroxylated solvent for a time sufficient to deposit a coating of a heterocyclic aromatic azole treating agent having up to 16 carbon atoms on the surface, and thereafter in sequence subjecting the coated surface to an anodizing bath and coating with a fatty acid having from 5 to 24 carbon atoms.

In this and like embodiments, there is included immersing the surface in an alcohol solution of the treating agent for 1 to 10 minutes; selecting benzotriazole-5-carboxylic acid or 2-mercaptobenzothiazole as the treating agent; selecting as the treating agent benzotriazole-5-carboxylic acid, and including, after anodizing, coating the surface with a 1–10% weight to volume solution of stearic acid in an alcohol; and selecting an immersion time of the surface in the treating agent solution of from 1 to 5 minutes.

In another embodiment, the invention provides the method of protecting series 1000, 2000 and 7000 copper-containing alloys of aluminum against surface corrosion, which includes dissolving a heterocyclic aromatic azole having up to 16 carbon atoms in an anodizing bath, at less than 100 millimole concentrations, anodizing the surface in the bath, and thereafter treating the anodized product with a fatty acid having from 5 to 24 carbon atoms dissolved in alcohol and therein using the treating agent. As in previous embodiments, in this embodiment, the treating agent azole is preferably selected from benzotriazole-5-carboxylic acid and 2-mercaptobenzothiazole as the treating agent, and after anodizing the surface, e.g. to an anodize oxide coat thickness between 0.2 and 0.6 mils, the surface is treated with a 1–12% weight to volume solution of stearic acid in an alcohol.

In another embodiment, the invention provides the method of protecting series 1000, 2000 and 7000 copper-containing alloys of aluminum against surface corrosion, by anodizing the surface and thereafter coating the anodized surface with a common hydroxylated solution of a heterocyclic aromatic azole having up to 16 carbon atoms and a fatty acid having from 5 to 24 carbon atoms, e.g. using solution concentrations in alcohol of the treating agent and the fatty acid between 0.5 and 10% weight to volume, selecting benzotriazole-5-carboxylic acid or 2-mercaptobenzothiazole as the treating agent, and after anodizing coating the surface with a 1–12% solution of stearic acid in isopropyl alcohol.

In addition to the foregoing methods, the invention provides surface protected aluminum products produced by the methods.

BEST MODE FOR CARRYING OUT THE INVENTION

As noted above, the invention provides methods for greatly enhancing the corrosion resistance of aluminum alloys with copper by use of a heterocyclic aromatic azole treating agent.

While not wishing to be bound to any particular theory, in aircraft structural alloys, such as 2024 T-3 in which copper is the principal alloying ingredient (copper 4.5%, Mg 1.5% and Mn 0.5%), anodizing forms copper-rich nanophases at the base metal/barrier layer interface. These nonstoichiometric phase boundary artifacts occur in debris fields of slip dislocations. These anomalous regions can significantly degrade both the corrosion and the fatigue resistance of anodized alloys. Corrosion results from anodic coupling of e.g. cathodic copper-rich areas to the base metal. Fatigue resistance degradation is due to mechanical fracturing and slipping at boundary layer/base metal interface. A sharp increase in corrosion or fatigue resistance should result in anodized systems if nonaluminum nanophases can be isolated from galvanic interaction with the surrounding base metal. In the present invention the azoles may sequester nonaluminum phases in the base metal/barrier layer interface and block anodic coupling, i.e. corrosion, between the base metal and other alloy constituents. The anodized oxide layer above this region is sealed with an ionogenic fatty acid sealant to prevent entry of corrosives into the barrier layer region. The invention thus provides a novel duplex means of increasing the corrosion resistance of structural aluminum alloys, by forming two chemically distinct, but interactive types of corrosion barriers.

EXAMPLES

The invention will be illustrated by the following examples wherein all parts are by weight to volume unless otherwise indicated.

Example 1

In this example, the test panel is precoated with the treating agent, anodized and then coated with the fatty acid.

A series of degreased panels (3"×10"×0.040") of 2024T-3 aluminum were dipped into a previously prepared, room temperature (60°–80° F.) 1% solution of benzotriazole-5-carboxylic acid in absolute isopropyl alcohol for periods ranging from 1 to 5 minutes. The panels were withdrawn and air dried. After two months of storage under ambient conditions, the panels were anodized in a hard anodizing bath electrolyte comprising 131 gm/l concentrated sulfuric acid, and 34.5 gm/l of oxalic acid in water under conditions of 36 amp/ft$^2$ and 38°–42° F. to oxide coat thickness of about 0.2 mils. Thereupon, a fatty acid coating was applied to the panels by applying a 1% stearic acid in isopropyl alcohol solution onto the panel surface. The protected surface was tested in a salt spray per ASTM B-117-90.

Showing corrosion was defined as five or more pits per panel in accordance with military specification MIL-A-8625E. No showing of corrosion (in fact no PITS) was detected after a remarkable 4030 hours of salt spray, when the test was discontinued. There was no difference in result depending on a 1 or 5 minute dip. Control specimens dipped less than 1 minute were not as resistant.

For comparison, panels only anodized showed corrosion after only 48 hours of salt spray testing. Panels anodized and treated with benzotriazole-5-carboxylic acid, but not subsequently coated with the fatty acid resisted showing corrosion for 72 hours of salt spray.

It will be seen therefore, that there is a large and synergistic improvement in the corrosion resistance of the test aluminum panels where both the noted treating agent and a fatty acid is employed. As seen in U.S. Pat. No. 5,169,458 medium to hard anodize followed by an alcohol solution coating of a fatty acid such as stearic will give 2856 hours of salt spray resistance, in contrast to the more than 4030 hours obtained by the use of the noted treating agent in addition to the fatty acid coating and anodize. on the panels was achieved without the use of environmentally-damaging chromates in the anodizing bath.

Example 2

Example 1 is duplicated substituting 2-mercaptobenzothiazole as the treating agent. Panels showed no corrosion for 3024 hours.

Example 3

Example 1 is duplicated using lauric acid as the fatty acid. Results are equivalent.

Example 4A and 4B

In this example, the treatment of the panel with the treating agent and the application of the anodize is effected simultaneously by adding the treating agent to the anodize bath.

A. Benzotriazole-5-carboxylic acid was added to anodizing electrolyte at a concentration of 0.033 gm/l. The electrolyte otherwise had the composition given in Example 1, and anodizing conditions were as in Example 1. Anodized oxide film thickness obtained was 0.2 mils.

B. Example 4A was repeated using soft anodize conditions including an electrolyte comprising 83.1 gm/l of concentrated sulfuric acid, 12 amp/ft$^2$ and temperatures of 69°–72° F. Anodized oxide coat thicknesses were either 0.2 mils or 0.4 mils.

The panels were coated with 1% stearic acid solution in absolute isopropyl alcohol by dipping. The panels all exceeded 4030 hours in salt spray testing.

Example 5

Example 4A was duplicated using isovaleric acid in alcohol solution (1%) in place of the stearic acid. The test panel exceeded 4030 hours in salt spray testing.

Example 6

Example 4A was duplicated using adipic acid in alcohol solution (1%) in place of the stearic acid. The test panel exceeded 4030 hours in salt spray testing.

Example 7

In this example, the treating agent is applied at the same time as fatty acid.

Panels anodized by the above noted hard anodize process, are washed with deionized water, and while wet immersed in a 1% absolute isopropyl alcohol solution of each of benzotriazole-5-carboxylic acid and stearic acid. Thereafter the panels are air dried. Corrosion resistance exceeded 4000 hours.

The foregoing examples illustrate that there are different methods of use of the invention, and this enables the ready introduction of the invention to existing production processes. Thus, as shown in the first embodiment above, the panels may be pretreated with the treating agent, and then stored for subsequent use, or, as in the second embodiment, existing anodizing baths may be modified by the addition of e.g. 2 pounds of treating agent to an 800 gallon tank of electrolyte, without adversely affecting the anodize or consuming undue amounts of the treating agent. Finally, where volatile (alcohol) organics may be a problem, the third embodiment can be used, wherein, after anodize, the parts are moved to a manufacturing area where alcohol recovery scrubbers are provided, for application of the treating agent and fatty acid in alcoholic solution followed by economical and safe recovery of the alcohol solvent for re-use.

Operating conditions are not narrowly critical. No special temperatures, atmospheres, or handling techniques are required. Conventional anodizing techniques and electrolytes can be used, with sulfuric acid baths, suitably with oxalic or other like acid added as well to prevent burn. Anodized oxide coat thicknesses after anodize are typically but not critically in the range of 0.2 to 0.6 mil. The amount of treating agent in the anodize bath should be about 1% +/−0.5 sufficient to incorporate an effective amount of the treating agent in the anodize coating. The pre- or post-anodize application of fatty acid, i.e. such acids having from 5 to 24 carbon atoms, is optimally from an alcoholic solution as described in U.S. Pat. No. 5,169,548, or from 1 to 12% weight to volume in the alcohol, preferably absolute isopropyl alcohol but more broadly any hydroxylated solvent having the property of adequately solvating the fatty acid and conditioning the anodize surface to render the fatty acid treatment effective as described in the present specification. The quantity of fatty acid coating is not narrowly critical, but should be the minimum effective amount; the quantity of heterocyclic aromatic azole treating agent also is not narrowly critical when applied from alcoholic solution. The alloys usefully processed in accordance with the present invention are alloys of aluminum and copper and other elements, with the copper being the second largest component of the alloy. Series 1000, 2000 and 7000 aluminum alloys are effectively treated, particularly those with from 0.2 to 7 per cent by weight copper content.

There is thus provided a versatile and highly effective means of greatly enhancing the corrosion resistance of coppercontaining aluminum alloys.

Other heterocyclic aromatic azoles which can be used include: benzoxazole, benzotriazole, benzimidazole, 2-mercapto-5-methyl benzimidazole, 2-mercaptoimidazole, and benzothiazole.

I claim:

1. Method of protecting copper alloys of aluminum against surface corrosion, comprising anodizing the aluminum surface to be protected, treating said surface with a heterocyclic aromatic azole treating agent having up to 16 carbon atoms before, during or after the anodizing step, and coating said treated surface after the anodizing step with a fatty acid of 5 to 24 carbon atoms.

2. Method of protecting copper alloys of aluminum of the 1000, 2000, or 7000 series against surface corrosion, comprising anodizing the aluminum surface to be protected, treating said surface with a heterocyclic aromatic azole treating agent having up to 16 carbon atoms before, during or after the anodizing step, and coating said treated surface after the anodizing step with a fatty acid of 5 to 24 carbon atoms.

3. The method of claim 1, further comprising anodizing said aluminum surface to an anodize layer thickness of 0.2 to 0.6 mils.

4. Method of protecting copper alloys of aluminum against surface corrosion, comprising anodizing the aluminum surface to be protected, treating said surface with benzotriazole-5-carboxylic acid treating agent before, during or after the anodizing step, and coating said treated surface after the anodizing step with a fatty acid of 5 to 24 carbon atoms.

5. The method of claim 1, further comprising treating said aluminum surface with an organic solution of said treating agent in advance of anodizing said surface.

6. The method of claim 1, further comprising selecting as said alloy a copper aluminum alloy containing from 0.2 to 7 per cent copper by weight, adding said treating agent to an anodizing bath, and anodizing said surface in said bath while simultaneously treating said surface with said treating agent.

7. The method of claim 1, further comprising treating said anodized surface with an organic solution of said treating agent after said anodizing step.

8. The method of claim 1, further comprising simultaneously treating said anodized surface with treating agent and coating said surface with said fatty acid.

9. The method of claim 1, further comprising forming a solution of both said treating agent and said fatty acid.

10. Method of protecting series 1000, 2000 and 7000 copper-containing alloys of aluminum against surface corrosion, comprising pretreating said surface with a 1 to 10% by weight solution in a hydroxylated solvent for a time sufficient to deposit a coating of a heterocyclic aromatic azole treating agent having up to 16 carbon atoms on said surface, and thereafter in sequence subjecting said coated surface to an anodizing bath and coating with a fatty acid having from 5 to 24 carbon atoms.

11. The method according to claim 10, further comprising immersing said surface in an alcohol solution of said treating agent for 1 to 10 minutes.

12. The method according to claim 11, further comprising selecting benzotriazole-5-carboxylic acid or 2-mercaptobenzothiazole as said treating agent.

13. The method according to claim 11, in which said treating agent is benzotriazole-5-carboxylic acid, and further comprising coating said surface with a 1–10% by weight solution of stearic acid in an alcohol after said anodizing.

14. The method according to claim 11, in which the immersion time of said surface in said treating agent solution is from 1 to 5 minutes.

15. Method of protecting series 1000, 2000 and 7000 copper-containing alloys of aluminum against surface corrosion, comprising dissolving a heterocyclic aromatic azole treating agent having up to 16 carbon atoms in an anodizing bath, anodizing bath, anodizing said surface in said bath, and thereafter coating said surface with a fatty acid having from 5 to 24 carbon atoms.

16. The method according to claim 15, further comprising using said treating agent at less than 100 millimole concentrations.

17. The method according to claim 16, further comprising selecting benzotriazole-5-carboxylic acid or 2-mercaptobenzothiazole as said treating agent.

18. The method according to claim 17, in which said treating agent is benzotriazole-5-carboxylic acid, and further comprising coating said surface with a 1–10% by weight solution of stearic acid in an alcohol after said anodizing.

19. The method according to claim 18, in which the anodize layer thickness is between 0.2 and 0.6 mils.

20. Method of protecting series 1000, 2000 and 7000 copper-containing alloys of aluminum against surface corrosion, comprising anodizing said surface and thereafter coating said anodized surface with a common hydroxylated solution of a heterocyclic aromatic azole treating agent having up to 16 carbon atoms and a fatty acid having from 5 to 24 carbon atoms.

21. The method according to claim 20, further comprising using solution concentrations of each of said treating agent and said fatty acid between 0.5 and 10% by weight to volume.

22. The method according to claim 20, further comprising selecting benzotriazole-5-carboxylic acid or 2-mercaptobenzothiazole as said treating agent.

23. The method according to claim 17, in which said treating agent is benzotriazole-5-carboxylic acid, and further comprising coating said surface with a 1–10% by weight solution of stearic acid in isopropyl alcohol after said anodizing.

24. The product of claim 1.

25. The product of claim 10.

26. The product of claim 15.

27. The product of claim 20.

* * * * *